(12) United States Patent
Scates

(10) Patent No.: US 8,703,868 B2
(45) Date of Patent: Apr. 22, 2014

(54) INTEGRATED PROCESS FOR PRODUCING POLYVINYL ALCOHOL OR A COPOLYMER THEREOF AND ETHANOL

(75) Inventor: Mark O. Scates, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 76 days.

(21) Appl. No.: 13/305,114

(22) Filed: Nov. 28, 2011

(65) Prior Publication Data

US 2013/0137819 A1     May 30, 2013

(51) Int. Cl.
    *C08F 8/00*         (2006.01)

(52) U.S. Cl.
    USPC ............... 525/62; 525/56; 526/75; 526/330; 526/331; 528/483; 528/490; 528/501

(58) Field of Classification Search
    USPC ......... 525/56, 62; 526/75, 330, 331; 528/483, 528/490, 501
    See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,268,299 A | 8/1966 | Russell |
| 3,478,112 A | 11/1969 | Karl et al. |
| 3,702,886 A | 11/1972 | Argauer et al. |
| 3,729,429 A | 4/1973 | Robson |
| 3,990,952 A | 11/1976 | Katzen et al. |
| 4,065,512 A | 12/1977 | Cares |
| 4,134,926 A | 1/1979 | Tsao et al. |
| 4,228,307 A | 10/1980 | Zimmerschied |
| 4,234,718 A | 11/1980 | Brown |
| 4,234,719 A | 11/1980 | Wan |
| 4,270,015 A | 5/1981 | Knifton |
| 4,275,228 A | 6/1981 | Gruffaz et al. |
| 4,317,918 A | 3/1982 | Takano et al. |
| 4,337,351 A | 6/1982 | Larkins |
| 4,352,940 A | 10/1982 | Adelman et al. |
| 4,374,265 A | 2/1983 | Larkins et al. |
| 4,395,576 A | 7/1983 | Kwantes et al. |
| 4,398,039 A | 8/1983 | Pesa et al. |
| 4,399,305 A | 8/1983 | Schreck |
| 4,421,939 A | 12/1983 | Kiff et al. |
| 4,443,639 A | 4/1984 | Pesa et al. |
| 4,463,138 A | 7/1984 | Wu et al. |
| 4,465,854 A | 8/1984 | Pond et al. |
| 4,471,136 A | 9/1984 | Larkins et al. |
| 4,480,115 A | 10/1984 | McGinnis |
| 4,497,967 A | 2/1985 | Wan |
| 4,517,391 A | 5/1985 | Schuster et al. |
| 4,521,630 A | 6/1985 | Wattimena et al. |
| 4,544,511 A | 10/1985 | Isshiki et al. |
| 4,550,185 A | 10/1985 | Mabry et al. |
| 4,581,473 A | 4/1986 | Polichnowski et al. |
| 4,613,700 A | 9/1986 | Maki et al. |
| 4,620,050 A | 10/1986 | Cognion et al. |
| 4,670,620 A | 6/1987 | Jacobs et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,820,767 A | 4/1989 | Wu |
| 4,826,795 A | 5/1989 | Kitson et al. |
| 4,843,170 A | 6/1989 | Isshiki et al. |
| 4,886,905 A | 12/1989 | Larkins et al. |
| 4,978,778 A | 12/1990 | Isshiki et al. |
| 4,985,572 A | 1/1991 | Kitson et al. |
| 4,990,655 A | 2/1991 | Kitson et al. |
| 5,008,235 A | 4/1991 | Wegman et al. |
| 5,061,671 A | 10/1991 | Kitson et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,198,592 A | 3/1993 | Van Beijnum et al. |
| 5,206,434 A | 4/1993 | Scates et al. |
| 5,241,106 A | 8/1993 | Inoue et al. |
| 5,243,095 A | 9/1993 | Roberts et al. |
| 5,306,845 A | 4/1994 | Yokohama et al. |
| 5,350,504 A | 9/1994 | Dessau |
| 5,414,161 A | 5/1995 | Uhm et al. |
| 5,475,144 A | 12/1995 | Watson et al. |
| 5,476,827 A | 12/1995 | Ferrero et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Bann, W.; Chemical Business Focus, Aug. 4, 2010, p. 1-34.*

(Continued)

*Primary Examiner* — Robert Jones, Jr.

(57) ABSTRACT

Ethanol is produced from methyl acetate by a hydrogenolysis reaction. The methyl acetate is produced as a byproduct during the conversion of a vinyl acetate polymer or copolymer to a polymer or copolymer of vinyl alcohol. By integrating the two processes, a valuable product, i.e. ethanol, is produced from a methyl acetate byproduct.

20 Claims, 1 Drawing Sheet

(56) References Cited

U.S. PATENT DOCUMENTS

| | | | |
|---|---|---|---|
| RE35,377 E | 11/1996 | Steinberg et al. | |
| 5,585,523 A | 12/1996 | Weiguny et al. | |
| 5,691,267 A | 11/1997 | Nicolau et al. | |
| 5,719,315 A | 2/1998 | Tustin et al. | |
| 5,731,456 A | 3/1998 | Tustin et al. | |
| 5,767,307 A | 6/1998 | Ramprasad et al. | |
| 5,770,770 A | 6/1998 | Kim et al. | |
| 5,821,111 A | 10/1998 | Gaddy et al. | |
| 5,849,657 A | 12/1998 | Rotgerink et al. | |
| 5,861,530 A | 1/1999 | Atkins et al. | |
| 5,945,570 A | 8/1999 | Arhancet et al. | |
| 5,973,193 A | 10/1999 | Crane et al. | |
| 6,049,008 A | 4/2000 | Roberts et al. | |
| 6,114,571 A | 9/2000 | Abel et al. | |
| 6,121,498 A | 9/2000 | Tustin et al. | |
| 6,204,417 B1 | 3/2001 | Fischer et al. | |
| 6,232,352 B1 | 5/2001 | Vidalin et al. | |
| 6,232,504 B1 | 5/2001 | Barteau et al. | |
| 6,294,703 B1 | 9/2001 | Hara et al. | |
| 6,462,231 B1 | 10/2002 | Yanagawa et al. | |
| 6,472,555 B2 | 10/2002 | Choudary et al. | |
| 6,486,366 B1 | 11/2002 | Ostgard et al. | |
| 6,495,730 B1 | 12/2002 | Konishi et al. | |
| 6,509,180 B1 | 1/2003 | Verser et al. | |
| 6,559,333 B1 | 5/2003 | Brunelle et al. | |
| 6,603,038 B1 | 8/2003 | Hagemeyer et al. | |
| 6,632,330 B1 | 10/2003 | Colley et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,696,596 B1 | 2/2004 | Herzog et al. | |
| 6,727,380 B2 | 4/2004 | Ellis et al. | |
| 6,765,110 B2 | 7/2004 | Warner et al. | |
| 6,768,021 B2 | 7/2004 | Horan et al. | |
| 6,812,372 B2 | 11/2004 | Janssen et al. | |
| 6,852,877 B1 | 2/2005 | Zeyss et al. | |
| 6,903,045 B2 | 6/2005 | Zoeller et al. | |
| 6,906,228 B2 | 6/2005 | Fischer et al. | |
| 6,927,048 B2 | 8/2005 | Verser et al. | |
| 7,005,541 B2 | 2/2006 | Cheung et al. | |
| 7,074,603 B2 | 7/2006 | Verser et al. | |
| 7,084,312 B1 | 8/2006 | Huber et al. | |
| 7,115,772 B2 | 10/2006 | Picard et al. | |
| 7,208,624 B2 | 4/2007 | Scates et al. | |
| 7,297,236 B1 | 11/2007 | Vander Griend et al. | |
| 7,351,559 B2 | 4/2008 | Verser et al. | |
| 7,375,049 B2 | 5/2008 | Hayes et al. | |
| 7,399,892 B2 | 7/2008 | Rix et al. | |
| 7,425,657 B1 | 9/2008 | Elliott et al. | |
| 7,468,455 B2 | 12/2008 | Mazanec et al. | |
| 7,507,562 B2 | 3/2009 | Verser et al. | |
| 7,538,060 B2 | 5/2009 | Barnicki et al. | |
| 7,553,397 B1 | 6/2009 | Colley et al. | |
| 7,572,353 B1 | 8/2009 | Vander et al. | |
| 7,608,744 B1 | 10/2009 | Johnston et al. | |
| 7,855,303 B2 | 12/2010 | Johnston et al. | |
| 7,863,489 B2 | 1/2011 | Johnston et al. | |
| 7,884,253 B2 | 2/2011 | Stites et al. | |
| 7,906,680 B2 | 3/2011 | Scates et al. | |
| 7,947,746 B2 | 5/2011 | Daniel et al. | |
| 2003/0013908 A1 | 1/2003 | Horan et al. | |
| 2003/0077771 A1 | 4/2003 | Verser et al. | |
| 2003/0104587 A1 | 6/2003 | Verser et al. | |
| 2003/0114719 A1 | 6/2003 | Fischer et al. | |
| 2003/0135070 A1 | 7/2003 | Picard et al. | |
| 2003/0191020 A1 | 10/2003 | Bharadwaj et al. | |
| 2004/0195084 A1 | 10/2004 | Hetherington et al. | |
| 2006/0019360 A1 | 1/2006 | Verser et al. | |
| 2006/0102520 A1 | 5/2006 | Lapinski et al. | |
| 2006/0106246 A1 | 5/2006 | Warner et al. | |
| 2006/0127999 A1 | 6/2006 | Verser et al. | |
| 2007/0191625 A1 | 8/2007 | Scates et al. | |
| 2007/0197822 A1 | 8/2007 | Picard et al. | |
| 2007/0270511 A1 | 11/2007 | Melnichuk et al. | |
| 2008/0207953 A1 | 8/2008 | Houssin et al. | |
| 2008/0221352 A1 | 9/2008 | Scates et al. | |
| 2008/0234512 A1 | 9/2008 | Picard et al. | |
| 2009/0005588 A1 | 1/2009 | Hassan et al. | |
| 2009/0023192 A1 | 1/2009 | Verser et al. | |
| 2009/0081749 A1 | 3/2009 | Verser et al. | |
| 2009/0166172 A1 | 7/2009 | Casey et al. | |
| 2009/0221725 A1 | 9/2009 | Chorney et al. | |
| 2009/0318573 A1 | 12/2009 | Stites et al. | |
| 2009/0326080 A1 | 12/2009 | Chornet et al. | |
| 2010/0016454 A1 | 1/2010 | Gracey et al. | |
| 2010/0029980 A1 | 2/2010 | Johnston et al. | |
| 2010/0029995 A1 | 2/2010 | Johnston et al. | |
| 2010/0030001 A1 | 2/2010 | Johnston et al. | |
| 2010/0030002 A1 | 2/2010 | Johnston et al. | |
| 2010/0113843 A1 | 5/2010 | Lee et al. | |
| 2010/0121114 A1 | 5/2010 | Johnston et al. | |
| 2010/0168466 A1* | 7/2010 | Johnston et al. | 560/261 |
| 2010/0168493 A1 | 7/2010 | Le Peltier et al. | |
| 2010/0196789 A1 | 8/2010 | Fisher et al. | |
| 2010/0204512 A1 | 8/2010 | Kimmich et al. | |
| 2010/0249479 A1 | 9/2010 | Berg-Slot et al. | |
| 2011/0004033 A1 | 1/2011 | Johnston et al. | |
| 2013/0137820 A1 | 5/2013 | Scates | |
| 2013/0137903 A1 | 5/2013 | Scates | |
| 2013/0137904 A1 | 5/2013 | Scates | |
| 2013/0137905 A1 | 5/2013 | Scates | |

FOREIGN PATENT DOCUMENTS

| | | |
|---|---|---|
| EP | 0087870 | 2/1983 |
| EP | 0104197 | 4/1984 |
| EP | 0108437 | 5/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0285786 | 10/1988 |
| EP | 0330853 | 9/1989 |
| EP | 0400904 | 5/1990 |
| EP | 0372847 | 6/1990 |
| EP | 0408528 | 7/1990 |
| EP | 0990638 | 4/2000 |
| EP | 1277826 | 1/2003 |
| EP | 2060553 | 5/2009 |
| EP | 2060555 | 5/2009 |
| EP | 2186787 | 5/2010 |
| EP | 1262234 | 12/2012 |
| GB | 1168785 | 10/1969 |
| GB | 1559540 | 1/1980 |
| GB | 2136704 | 9/1984 |
| JP | 4913304 | 7/1992 |
| JP | 6116682 | 4/1994 |
| JP | 10-306047 | 11/1998 |
| JP | 11-147845 | 6/1999 |
| JP | 2001-046874 | 2/2001 |
| JP | 2001-157841 | 6/2001 |
| WO | WO 82/03854 | 11/1982 |
| WO | WO 83/03409 | 10/1983 |
| WO | WO 03/040037 | 5/2003 |
| WO | WO 2005/102513 | 11/2005 |
| WO | WO 2009/009322 | 1/2009 |
| WO | WO 2009/009323 | 1/2009 |
| WO | WO 2009/063176 | 5/2009 |
| WO | WO 2009/086839 | 7/2009 |
| WO | WO 2009/105860 | 9/2009 |
| WO | WO 2010/014145 | 2/2010 |
| WO | WO 2010/014151 | 2/2010 |
| WO | WO 2010/014153 | 2/2010 |
| WO | WO 2010/055285 | 5/2010 |

OTHER PUBLICATIONS

Salyer, I.O., et al.; Journal of Polymer Science: Part A-1, 1971, p. 3083-3103.*

Yang, et al., "Process of Ethanol Synthesis through Esterification of Acetic Acid and Economic Analysis", No. 4, 2011.

(56) References Cited

OTHER PUBLICATIONS

ZeaChem, Inc., Technology Overview, Lakewood, Colorado www.zeachem.com, 2008.

Subramani et al., "A Review of Recent Literature to Search for an Efficient Catalytic Process for the Conversion of Syngas to Ethanol," Energy & Fuels, 2008, vol. 22, pp. 814-839.

Spivey et al., "Heterogeneous catalytic synthesis of ethanol from biomass-dervied syngas," Chemical Society Review, 2007, vol. 36, pp. 1514-1528.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., Reactions of Carboxylic Acids on Oxides, Journal of Catalysis 168:255-264 (1997).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21ST NAM San Francisco, CA, Jun. 10, 2009.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Brunauer Emmett and Teller, J. Am. Chem. Soc. 60, 309 (1938).

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

Proc. Roy Soc. A314, pp. 473-498 (1970).

Djerboua, et al., "On the performance of a highly loadedCO/SiO2 catalyst in the gas phase hydrogenation of crotonaldehyde thermal treatments—catalyst structure-selectivity relationship," Applied Catalysis A: General (2005), 282, p. 123-133.

Liberkova, and Tourounde, "Performance of Pt/SnO2 catalyst in the gas phase hydrogenation of crotonaldehyde," J. Mol. Catal. A: Chemical (2002), 180, p. 221-230.

Rodrigues and Bueno, "Co/SiO2 catalysts for selective hydrogenation of crotonaldehyde: III. Promoting effect of zinc," Applied Catalysis A: General (2004), 257, p. 210-211.

Ammari, et al. "An emergent catalytic material: Pt/ZnO catalyst for selective hydrogenation of crotonaldehyde," J. Catal. (2004), 221, p. 32-42.

Ammari, et al. "Selective hydrogenation of crotonaldehyde on Pt/ZnCl2/SiO2 catalysts," J. Catal. (2005), 235, p. 1-9.

Consonni, et al. "High Performances of Pt/ZnO Catalysts in Selective Hydrogenation of Crotonaldehyde," J. Catal. (1999), 188, p. 165-175.

Nitta, et al. "Selective hydrogenation of $\alpha\beta$-unsaturated aldehydes on cobalt—silica catalysts obtained from cobalt chrysotile," Applied Catal. (1989), 56, p. 9-22.

W. S. Park, et al., Journal of Polymer Science, Polymer Physics Ed., vol. 15, p. 81 (1977).

International Search Report and Written Opinion for PCT/US2009/004197 mailed Mar. 24, 2010 (10 pages).

International Search Report and Written Opinion for PCT/US2009/004195 mailed Mar. 26, 2010 (12 pages).

International Search Report and Written Opinion for PCT/US2010/022947 mailed Jun. 7, 2010.

International Search Report and Written Opinion for PCT/US2010/022949 mailed Jun. 7, 2010.

Invitation to Pay Fees and Partial Search Report for PCT/US2010/022950 mailed Jun. 15, 2010.

International Search Report and Written Opinion for PCT/US2010/022950 mailed Sep. 7, 2011.

International Search Report and Written Opinion for PCT/US2010/022953 mailed Jun. 7, 2010.

International Search Report and Written Opinion for PCT/US2010/054134 mailed Feb. 28, 2011 (02001).

K. Noro, "Polyvinyl Alcohol by Acetate", 1976, pp. 303-307 and "6 Polyvinyl Alcohol", pp. 95-130.

International Search Report and Written Opinion mailed Mar. 1, 2013 in corresponding International Application No. PCT/US2012/065851.

Zheng, et al., (2007). Preparation and catalytic properties of a bimetallic Sn-Pt complex in the supercages of NaY zeolite by use of surface organometallic chemistry, Applied Organometallic Chemistry, 21(10), 836-840.

\* cited by examiner

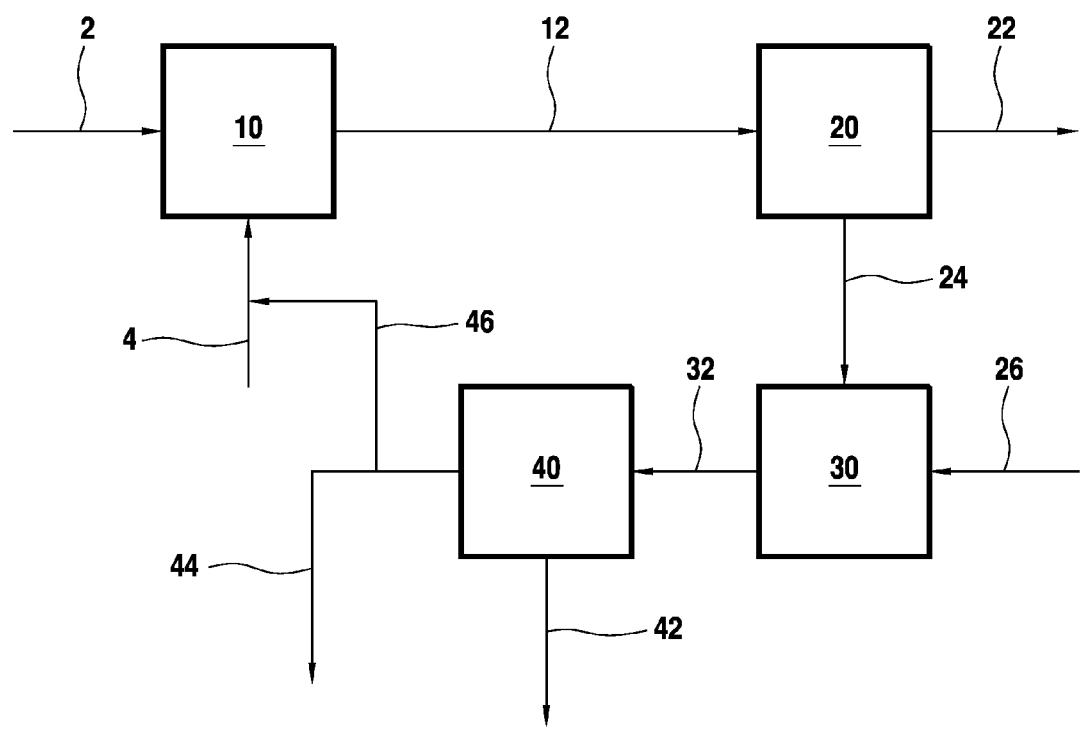

INTEGRATED PROCESS FOR PRODUCING POLYVINYL ALCOHOL OR A COPOLYMER THEREOF AND ETHANOL

FIELD OF THE INVENTION

The present invention relates generally to processes for producing ethanol and, in particular, to a process for making ethanol from methyl acetate, which is produced during the conversion of a vinyl acetate polymer or copolymer to a vinyl alcohol polymer or copolymer.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature.

Other processes for producing ethanol have also been proposed. EP2060553, for example, describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

The need remains for processes for making ethanol, especially from sources, which would otherwise be treated as byproducts in industrial manufacture.

SUMMARY OF THE INVENTION

The present invention relates to processes for making ethanol. In one embodiment, the invention is a process for producing ethanol comprising reacting methyl acetate with hydrogen to form methanol and ethanol. This reaction of methyl acetate with hydrogen to form methanol and ethanol is referred to herein as a hydrogenolysis reaction. The methyl acetate is produced by contacting a vinyl acetate based polymer or copolymer with a base and methanol under conditions effective to form a polymer or copolymer of vinyl alcohol and a first stream comprising methyl acetate. At least a portion of the methyl acetate coproduced with the vinyl alcohol polymer or copolymer is used as a feed to the hydrogenolysis reaction.

Thus, in one embodiment, the invention is to a process for producing ethanol, the process comprising the steps of: (a) contacting a vinyl acetate based polymer or copolymer with a base and methanol under conditions effective to form a polymer or copolymer of vinyl alcohol and a first stream comprising methyl acetate; and (b) reacting at least a portion of the methyl acetate with hydrogen to form methanol and ethanol. In an optional step (c), at least a portion of the methanol produced in step (b) may be recycled to the contacting step (a). Examples of the vinyl acetate based polymer or copolymer used in step (a) include polyvinyl acetate (PVAc) and an alkene vinyl acetate copolymer, such as ethylene vinyl acetate (EVAc). Examples of the vinyl alcohol polymer or copolymer formed in step (a) include polyvinyl alcohol (PVOH) and an alkene vinyl alcohol copolymer, such as ethylene vinyl alcohol (EVOH). For example, in step (a), polyvinyl acetate may be converted to polyvinyl alcohol, and an alkene vinyl acetate copolymer may be converted into an alkene vinyl alcohol copolymer.

The vinyl acetate polymer or copolymer may be formed by polymerizing vinyl acetate monomer, optionally in the presence of a comonomer, such as an alkene, e.g., ethylene. The vinyl acetate monomer may be formed through the acetoxylation of ethylene. Thus, the process may further comprise the steps of: (d) contacting acetic acid with reactants, e.g., ethylene and oxygen, under conditions effective to form vinyl acetate; and (e) contacting the vinyl acetate with reactants under conditions effective to form the vinyl acetate based polymer or copolymer, such as polyvinyl acetate or an alkene vinyl acetate copolymer.

The first stream comprising methyl acetate from step (a) may be purified to remove at least some impurities, which may be detrimental to the hydrogenolysis reaction. This purification may take place by a variety of techniques, including extractive distillation, liquid/liquid extraction, distillation, crystallization, gas stripping, a membrane separation technique, filtration, flash vaporization, chemical reaction of one or more impurities, and combinations of these techniques. Thus, the process may further comprise the step of purifying the first stream comprising methyl acetate from step (a) to form a second stream comprising methyl acetate. The purifying step may remove sufficient impurities from the first stream such that the second stream is a more suitable feed to a hydrogenolysis process to produce methanol and ethanol.

The first stream comprising methyl acetate and impurities from step (a) may comprise methyl acetate and impurities, such as methanol, light organics, water, vinyl acetate monomer, acetaldehyde, dimethylacetyl, sodium acetate, and polymer solids. The second stream obtained by purifying the second stream may comprise methyl acetate and impurities, such as methanol and water.

The purified second stream may comprise methanol in a wide range of quantities, depending upon a number of factors, including the manner in which PVOH is made and the manner in which methyl acetate is recovered and purified. A particular source methanol in admixture with methyl acetate is from excess methanol used in a methanolysis reaction with polyvinyl acetate. The second stream may comprise, for example, from 5 wt % to 95 wt %, for example, from 60 wt % to 95 wt %, for example, from 70 wt % to 90 wt %, methyl acetate and from 5 wt % to 95 wt %, for example, from 5 wt % to 40 wt %, for example, from 10 wt % to 30 wt %, methanol, based on the total weight of methyl acetate and methanol in the second stream.

The purified second stream may also comprise water in a wide range of quantities, depending upon a number of factors, including the manner in which methyl acetate is recovered and purified. However, it is preferred that the second stream contains no more than a small amount of water, so that the ethanol recovered from the subsequent hydrogenolysis also contains a small amount of water. For example, the second stream may comprise from 90 wt % to 100 wt %, for example, from 93 wt % to 100 wt %, for example, from 95 wt % to 100 wt %, methyl acetate and from 0 wt % to 10 wt %, for example, from 0 wt % to 7 wt %, for example, from 0 wt % to 5 wt %, for example, from 0 wt % to 5 wt %, water, based on the total weight of methyl acetate and water in the second stream.

The hydrogenolysis reaction may take place in the presence of a suitable hydrogenolysis catalyst. Examples of hydrogenolysis catalysts include copper containing catalysts, especially those with copper in a reduced or partially reduced state. Examples of such copper containing catalysts are described in U.S. Pat. No. 5,198,592, U.S. Pat. No. 5,414,161, U.S. Pat. No. 7,947,746, U.S. Patent Application Publication No. US 2009/0326080, and WO 83/03409, the entireties of which are incorporated herein by reference.

After methanol and ethanol are produced by hydrogenolysis, the methanol and ethanol may be separated by a suitable separation technique, such as distillation, to form an ethanol stream and a methanol stream. The ethanol stream may comprise at least 90 wt. % ethanol, for example, at least 92 wt. % ethanol, for example, at least 95 wt. % ethanol. The methanol stream may comprise at least 90 wt. % methanol, for example, at least 92 wt. % methanol, for example, at least 95 wt. % methanol. The methanol stream may be recycled to step (a) for contact with a vinyl acetate based polymer or copolymer.

In another embodiment, the invention is to a process for producing ethanol comprising the hydrogenolysis of methyl acetate derived from a vinyl alcohol polymer or copolymer production facility to form methanol and ethanol, and optionally recycling the methanol to the production facility.

BRIEF DESCRIPTION OF THE DRAWING

FIG. 1 is a representation of an integrated process for producing polyvinyl alcohol or a copolymer thereof and ethanol.

DETAILED DESCRIPTION OF THE INVENTION

A. Introduction

Polyvinyl alcohol is commercially produced by the reaction of vinyl acetate with a radical initiator to produce polyvinyl acetate. Polyvinyl acetate may then be reacted with methanol in the presence of a base under conditions sufficient to produce polyvinyl alcohol (PVOH) and methyl acetate. Copolymers of polyvinyl alcohol such as ethylene/vinyl alcohol copolymers (EVOH) may be similarly formed by reacting an ethylene/vinyl acetate copolymer with methanol in the presence of a base under conditions sufficient to form the EVOH and methyl acetate. Thus, in both reactions, methyl acetate is produced as a byproduct. According to the present invention, methyl acetate formed in the production of PVOH or EVOH may be subjected to hydrogenolysis in the presence of a catalyst to form methanol and ethanol. The methanol preferably is recycled to the step for producing the PVOH or EVOH. Thus, the present invention may be described as an integrated process for producing both (1) polyvinyl alcohol polymer or copolymer and (2) ethanol.

FIG. 1 provides a flow diagram of an example of an integrated process for producing polyvinyl alcohol or a copolymer thereof and ethanol. It will be understood that lines depicted in FIG. 1, such as lines 2, 12 and 22, depict flow of materials through the process, rather than specific apparatus or equipment, such as pipes. In FIG. 1, a feed comprising polyvinyl acetate or an ethylene/vinyl acetate copolymer is introduced through line 2 into an alcoholysis reaction zone 10. Another feed comprising methanol is also introduced into the alcoholysis reaction zone 10 through line 4. Optionally, the polyvinyl acetate or an ethylene/vinyl acetate copolymer and methanol may be premixed before being introduced into the alcoholysis reaction zone 10. A suitable catalyst may also be introduced into the alcoholysis reaction zone 10, for example, along with the methanol feed in line 4 or through a line not shown in FIG. 1.

Line 12 represents the transfer of alcoholysis reaction product to product recovery zone 20. A product comprising polyvinyl alcohol or ethylene/vinyl alcohol copolymer is recovered via line 22, and a methyl acetate stream is removed from product recovery zone 20 via line 24. The methyl acetate stream 24 is introduced into hydrogenolysis zone 30. Also, a feed comprising hydrogen is introduced into hydrogenolysis zone 30 via line 26. The product stream 32 passes from the hydrogenolysis zone 30 to separation zone 40. An ethanol product stream 42 removes ethanol product from separation zone 40, and a methanol product stream 44 removes methanol product from separation zone 40. Optionally, a portion or all of the methanol product stream may be diverted via side stream 46 for recycle to alcoholysis zone 10, for example, by introduction into methanol feed in line 4 or by direct introduction into the alcoholysis zone 10 by lines not shown in FIG. 1.

B. Production of Vinyl Alcohol Polymers and Copolymers

The production of PVOH or copolymers of PVOH from vinyl acetate involves two steps. The first step is the polymerization of vinyl acetate to form polyvinyl acetate, and the second step involves alcoholysis of the polyvinyl acetate to form PVOH. The first step involves the conversion of vinyl acetate into repeating polymeric units. This conversion may be depicted schematically as follows:

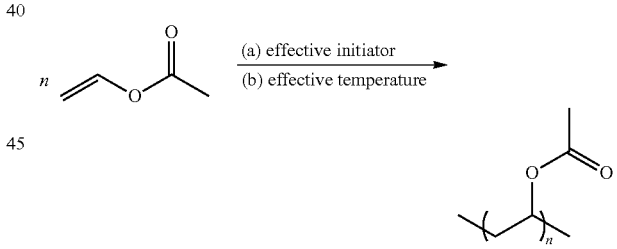

wherein n is an integer of from about 2500 to 25,000, preferably from about 9000 to about 23,000, and most preferably from about 11,000 to about 21,000. The first step of the process can be conveniently carried out by bulk polymerizing vinyl acetate in the presence of an initiator to form the desired polyvinyl acetate. The polymerization process optionally occurs in the presence of a co-monomer such as ethylene to form a copolymer of ethylene/vinyl acetate. Exemplary processes for forming PVOH are described in U.S. Pat. No. 4,463,138; and U.S. Pat. No. 4,820,767, each of which is incorporated herein by reference in its entirety.

Vinyl acetate, which is also referred to in the art as vinyl acetate monomer (VAM), may be prepared by contacting acetic acid with reactants under conditions effective to form vinyl acetate. In one embodiment, acetic acid is reacted with ethylene and oxygen to form vinyl acetate. Examples of such reactions are described in U.S. Pat. No. 7,855,303 and in U.S.

Pat. No. 7,468,455, the entireties of which are incorporated herein by reference. In another embodiment, acetic acid reacted with acetylene to form vinyl acetate. An example of such a reaction is described in U.S. Pat. No. 3,268,299, which is also incorporated herein by reference.

The initiator may be a free radical polymerization initiator that is capable of bulk polymerizing vinyl acetate at a temperature of from about 0° C. to about 40° C. to provide an essentially linear polyvinyl acetate having a weight average molecular weight equal to or greater than about 900,000, which on alcoholysis provides a PVOH having a weight average molecular weight equal to or greater than about 450,000. The weight average molecular weight is determined by the method described in W. S. Park, et al, Journal of Polymer Science, Polymer Physics Ed. vol. 15, p. 81 (1977). Usually, the effective initiator is an azo compound having a half life of up to about 200 hrs at a temperature of from about 0° C. to about 40° C. In a preferred embodiment of the invention, the initiator will have a half life of from about 1 to about 200 hours at a temperature of from about 0° C. to about 40° C., and in the particularly preferred embodiments of the invention, the initiator of choice will have a half life of from about 10 to about 150 hours at a temperature of from about 10° C. to about 35° C. In one aspect, the initiator has a half life of from about 50 to about 100 hours measured at a temperature of from about 15° C. to about 30° C. The half life of the initiator can be calculated from the decomposition rate of the initiator which is described in, for example, the "Polymer Handbook", J. Brandrup & E. H. Immergut, John Wiley & Sons. 1975. Illustrative of initiators suitable for use in the procedure of the invention are azo compounds of the formula:

wherein $R_1$ and $R_2$ are the same or different, and are independently straight or branched-chain lower alkyl, lower alkoxyalkyl, cycloalkyl, nitrile substituted alkyl groups, or phenylalkylnitrile. The selection of suitable $R_1$ and $R_2$ groups is well within the skill of the art. Within the scope of the above formula preferred azo initiator are 2,2'-azobis-(2,4-dimethyl-4-methoxyvaleronitrile); 2,2'-azobis-(2,4-dimethylvaleronitrile); 1,1'-azobis-1-cyclooctanenitrile; azobis-2-methylbutyronitrile; 1,1'-azobis-1-cyclohexanecarbonitrile; 2,2'-azobis-2-propylbutyronitrile; 2,2'-azobis-2-methylhexylonitrile; 2,2'-azobis-2-benzylpropionitrile and the like.

There is a relationship between the amount of initiator employed, the polymerization temperature and polymerization times. Each of the aforementioned process parameters may be selected, if desired, to maximize the molecular weight of the polyvinyl acetate, and, if desired, to minimize the degree of branching. In some exemplary embodiments, the initiator concentration may vary from about $1 \times 10^{-6}$ to about $1 \times 10^{-3}$ mole percent based on the total moles of vinyl acetate monomer, the polymerization temperature may range from about 0° C. to about 40° C., and polymerization times may vary from about 2 to about 48 hrs. In another aspect, initiator concentration will vary from about $1 \times 10^{-5}$ to about $1 \times 10^{-3}$ mole percent on the aforementioned basis, polymerization temperatures will vary from about 10° C. to about 35° C., and polymerization times will vary from about 4 to about 36 hrs. In another aspect, initiator concentration will vary from about $2 \times 10^{-5}$ to about $2 \times 10^{-4}$ mole percent on the aforementioned basis, polymerization temperatures will vary from about 15° C. to about 25° C., and polymerization times will vary from about 6 to about 24 hrs. In yet another aspect, the initiator concentration will vary from about $5 \times 10^{-5}$ to about $5 \times 10^{-4}$ mole percent on the aforementioned basis, polymerization temperatures will vary from about 15° C. to about 25° C. and polymerization times will vary from about 6 to about 18 hrs.

The vinyl acetate monomer optionally has a purity equal to or greater than about 99% by weight and preferably equal to or greater than about 99.9% by weight. Small scale quantities of vinyl acetate having a purity equal to or greater than about 99.9% by weight may be obtained by fractionating vinyl acetate monomer with a 200-plate spinning band column and collecting the middle boiling fraction to about 72.2° C. Large quantities of vinyl acetate having a purity equal to or greater than 99.9% by weight for industrial production of high molecular weight PVOH may be obtained by standard industrial distillation procedures which are well known to those having skill in the art.

Polymerization of the vinyl acetate monomer is accomplished by initiated radical polymerization. Oxygen acts as an inhibitor of radical polymerization and, accordingly, the polymerization is preferably carried out under substantially oxygen free condition. Thus, the fractionated highly pure vinyl acetate monomer is preferably subjected to deoxygenation procedures prior to polymerization. This may be accomplished by a freeze-thaw operation under a high vacuum and an inert gas sweep wherein the monomer is frozen at about –93° C., thawed, refrozen, thawed, etc. The vinyl acetate monomer may be subjected to at least about three freeze-thaw cycles in order to ensure an essentially complete removal of oxygen. However, removal of oxygen by bubbling pure nitrogen through the polymerization mixture may also be also adequate.

Once a purified and deoxygenated vinyl acetate monomer is obtained, the monomer may then be transferred to a suitable reactor for conducting the free radical bulk polymerization process. Reactors suitable for use in the polymerizing reaction are not critical, and reactors used in conventional bulk polymerizations can be used. Suitable reactors will usually be equipped with a temperature control means to maintain the reaction mixture within the desired temperature range and should also be equipped with means to maintain the reactor substantially oxygen free; as for example, means for carrying out the polymerization under an inert gas such as nitrogen.

The polymerization process can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible runaway reaction temperatures or fluctuations therein. In preferred embodiments of the process, agitation means to vary the degree of mixing of the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and reagents may be initially introduced into the reaction zone batchwise or may be continuously or intermittently introduced in such zone during the course of the process. Means to introduce and/or adjust the quantity of reactants introduced, either intermittently or continuously into the reaction zone during the course of the reaction, can be conveniently utilized in the process especially to maintain the desired molar ratio of the reaction solvent, reactants and reagents.

Upon completion of the polymerization process, unreacted vinyl acetate may be removed by distillation under atmospheric or sub-atmospheric pressures. A polymeric residue comprising polyvinyl acetate will remain in the vessel utilized for the removal of unreacted vinyl acetate. The polyvinyl acetate product may be worked up by conventional means, as for example by initially dissolving the polymeric residue in an organic solvent such as acetone, tetrahydrofuran, methanol, dichloromethane, ethyl acetate, etc., and then precipitating the polymer with a non-solvent such as hexane, cyclohexanol, diethyl ether, mesitylene or the like. Similarly, precipitation of the polymers may be accomplished by simply employing cold water. Recovery of the polymer is then accomplished by standard filtration and drying procedures.

Polyvinyl acetate produced by the above process will have an intrinsic viscosity, and thus a corresponding molecular weight which is only slightly higher than reacetylated polyvinyl acetate produced from PVOH resulting from alcoholysis of the original polyvinyl acetate. Thus, the polyvinyl acetate that is produced may be essentially linear. Polyvinyl acetate produced in accordance with this process may have an intrinsic viscosity that is equal to or greater than about 3.2 dL/g. This corresponds to a weight average molecular weight of equal to or greater than about $1.0 \times 10^6$. Thus, given the fact that the repeat unit of polyvinyl acetate has a molecular weight of about 86 and the repeating unit of PVOH has a molecular weight of about 44, PVOH produced by the alcoholysis of such polyvinyl acetate has a weight average molecular weight of at least about $0.45 \times 10^6$. In a preferred embodiment of the invention, the polyvinyl acetate has an intrinsic viscosity ranging from about 3.5 dL/g to about 4.0 dL/g. Polyvinyl acetate falling within this intrinsic viscosity range has a weight average molecular weight ranging from about $1.3 \times 10^6$ to about $1.6 \times 10^6$, and PVOH prepared by the alcoholysis of this material will have a weight average molecular weight ranging from about $0.5 \times 10^6$ to about $0.8 \times 10^6$.

The determination of the weight average molecular weight of polyvinyl acetate may be accomplished by any one of a number of techniques known to those skilled in the art. Illustrative examples of suitable means for conducting the molecular weight determination include light scattering techniques which yield a weight average molecular weight and intrinsic viscosity determination which may be correlated to weight average molecular weight in accordance with the relationship $[\eta]=5.1 \times 10^{-5} M^{0.791}$ described more fully by W. S. Park, et al. in the Journal of Polymer Science, Polymer Physics Ed., vol. 15, p. 81 (1977).

The second step, converting polyvinyl acetate to PVOH, can be depicted schematically as follows:

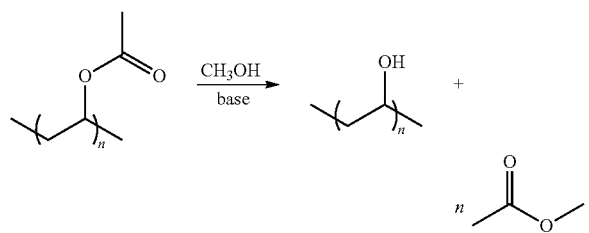

wherein n is as described above. Conventional procedures for the alcoholysis of polyvinyl acetate can be used to convert the polyvinyl acetate into PVOH. Illustrative of such procedures are those described in detail in U.S. Pat. No. 4,463,138 which is incorporated herein by reference. Briefly stated, the alcoholysis may be accomplished by initially dissolving the polyvinyl acetate in a quantity of a low molecular weight alcohol such as methanol sufficient to form at least about a 2% solution of the polyvinyl acetate resin. Base or acid catalysis may then be employed in order to convert the polyvinyl acetate to PVOH which is produced in the form of a gel. Base catalysis is preferred, however, with suitable bases including anhydrous potassium hydroxide, anhydrous sodium hydroxide, sodium methoxide, potassium methoxide, etc. The alcoholysis reaction may take place under anhydrous or substantially anhydrous conditions, for example, when sodium hydroxide is used as the base, to avoid unwanted formation of sodium acetate instead of the desired methyl acetate. The gel material is optionally chopped into small pieces and may be extracted repeatedly with methanol, ethanol or water for removal of residual base salts. The essentially pure PVOH may be dried under vacuum at a temperature of about 30° C. to about 70° C. for about 2 to 20 hours. PVOH produced in accordance with the process may have a weight average molecular weight of at least about $0.45 \times 10^6$. In a preferred embodiment, the weight average molecular weight of the PVOH is from about $0.45 \times 10^6$ to about $1.0 \times 10^6$, e.g., from about $0.5 \times 10^6$ to about $0.8 \times 10^6$.

PVOH produced in accordance with this invention may be useful in the production of PVOH fibers of excellent strength. Also, fibers produced from the PVOH of this invention preferably have high melting points.

The above-described alcoholysis reaction may be similarly employed in the formation of copolymers of polyvinyl alcohol, and in particular, in the alcoholysis of ethylene/vinyl acetate copolymer to form EVOH.

C. Methyl Acetate Stream

As shown above, for each molar equivalent of the repeating units of the polyvinyl acetate, the alcoholysis reaction forms one mole of methyl acetate byproduct. U.S. Pat. No. 7,906,680, the entirety of which is incorporated herein by reference, describes a process for coproducing polyvinyl alcohol or an alkene vinyl alcohol copolymer and acetic acid. In the process, the methyl acetate byproduct from the formation of the polyvinyl alcohol or an alkene vinyl alcohol copolymer is carbonylated to form acetic acid and/or acetic anhydride. In another process described in U.S. Pat. No. 7,906,680, the methyl acetate is converted to acetic acid by hydrolysis. The acetic acid is then sold or can be recycled to vinyl acetate production. The processes of the present invention advantageously involve directing the methyl acetate to a hydrogenolysis step, described below, to produce ethanol and methanol. The processes of the present invention thereby reduce or eliminate the need for hydrolysis equipment and concomitant energy requirements.

The methyl acetate stream that is derived from the polyvinyl alcohol or an alkene vinyl alcohol copolymer production process may contain various components that render the methyl acetate stream unsuitable or less suitable for being directly fed to the hydrogenolysis process. The methyl acetate stream may comprise, for example, methyl acetate, methanol (excess reactant in the above mentioned reaction), light organic impurities, sodium acetate, vinyl acetate monomer, and potentially polymer solids and water. Light organic impurities contained in the crude methyl acetate stream obtained in the conversion of vinyl acetate polymer or copolymer to vinyl alcohol polymer or copolymer may include, for example, carbonyl impurities such as acetic acid, acetaldehyde, acetone, methyl ethyl ketone, butyraldehyde, crotonaldehyde, 2-ethyl crotonaldehyde, and 2-ethyl butyraldehyde and the like, as well as unsaturated aldehydes. Additional impurities, which may be present in the methyl acetate stream, may include toluene, benzene, dimethylacetal, 3-methyl-2-pentanone, propionic acid, ethyl acetate and ethanol.

Depending on the amount and type of the various contaminants in the methyl acetate stream as well as the catalyst sensitivity in the hydrogenolysis step, it may be desired to remove some of the contaminants contained in the methyl acetate stream prior to sending the stream to the hydrogenolysis step. The presence of polymer solids in the methyl acetate stream, for example, may interfere or foul the hydrogenolysis reactor and are preferably removed from the methyl acetate stream before hydrogenolysis. In addition, the water content of the methyl acetate stream may be adjusted as part of purification of the methyl acetate stream prior to hydrogenolysis.

Methods to purify the crude methyl acetate stream include, but are not limited to, separation of water, impurities and solids via extractive distillation, liquid/liquid extraction, distillation, crystallization, gas stripping, a membrane separation technique, filtration, flash vaporization, and chemical reaction of one or more impurities. One way of using a chemical reaction to remove impurities from a methyl acetate stream is described in U.S. Patent Publication No. 2010/0204512, where the aldehyde content of a stream is reduced by contacting the stream with a catalyst comprising a Group VIII to XI metal, such as platinum or palladium. Another way of using a chemical reaction to remove impurities from a methyl acetate stream is described in U.S. Pat. No. 5,206,434, where carbonyl impurities in a stream are reduced by adding an amino compound, such as hydroxylamine sulfate to the stream under conditions sufficient to react the amino compound with carbonyl impurities to form a water soluble nitrogenous derivative.

In the production of PVOH or copolymer thereof, the resultant methyl acetate formed may be considered to be a mother liquor to be ultimately purified and fed to a methyl acetate hydrogenolysis reactor for the production of ethanol and methanol. The crude methyl acetate stream may be directed to a mother liquor column for purification to remove impurities, such as light organic components, polymeric solids and water. The column may be operated at elevated pressure, and heated, to remove essentially all of the methyl acetate in an overhead stream in purified form, and over 95% of the methanol from the impure methyl acetate crude mixture. The reflux of the column may be adjusted to control the amount of water in the column overhead. The polymeric solids may comprise polyvinyl acetate, PVOH, and sodium acetate. These polymeric solids may exit from the bottom of the mother liquor column as a residue.

By operating the mother liquor column at an elevated pressure, the overhead components or overheads may be used as a heat source for other recovery columns in the PVOH plant. Operating at about 55 psig allows for over 50% of the energy used in this tower to be recovered. Other streams may additionally be sent to the mother liquor column for separation. For example, a stream containing water and methanol from the extractive distillation of vinyl acetate and methanol, which is often used in the PVOH process, may also be sent to the mother liquor column for separation.

Thus, an initial or crude methyl acetate stream from the polyvinyl alcohol polymer or copolymer production process may be recovered and refined to form a refined methyl acetate stream, which is more suitable for being fed to a methyl acetate hydrogenolysis process. The initial or crude methyl acetate stream is also referred to herein as a first methyl acetate stream, and the refined stream is also referred to herein as a second methyl acetate stream. The second stream contains less impurities, which could adversely affect the hydrogenolysis reaction.

Excess water and polymer solids may be removed while organic losses in the aqueous stream are kept to a low level. Other aqueous/organic streams which contain a subset of the above listed components may also be purified. The product of the purification step is a refined methyl acetate stream, also referred to herein as a second stream, generally containing methyl acetate, and an acceptable level of impurities such as methanol, essentially no polymer solids, and sufficiently low amounts of water. The refined methyl acetate stream may comprise, for example, methanol in an amount of 5 wt % to 95 wt %, for example, 5 wt % to 40 wt %, for example, 10 wt % to 30 wt % methanol, based on the total weight of methanol and methyl acetate in the refined methyl acetate stream. This refined methyl acetate stream may also comprise, for example, water in an amount of 0 wt % to 10 wt %, for example, 0 wt % to 7 wt %, for example, 0 wt % to 5 wt % water, based on the total weight of water and methyl acetate in the refined methyl acetate stream. The impurities or amounts thereof, including water concentration, can vary based on the desired application, hydrogenolysis catalyst employed and the equipment in use.

D. Hydrogenolysis

As discussed above, the processes of the invention involve a step of subjecting methyl acetate derived from a PVOH or PVOH copolymer (e.g., EVOH) to hydrogenolysis in a hydrogenolysis reactor to form methanol and ethanol. In this context, the term "hydrogenolysis" of methyl acetate refers to the reaction of methyl acetate with hydrogen to form methanol and ethanol, but it should be understood that this reaction is not limited to any particular mechanism and may occur via one or more intermediates, e.g., acetic acid, which may undergo further reaction, e.g., hydrogenation, to form one or more alcohol species, e.g., ethanol.

The invention may be described in relation to the production of ethanol, but, as indicated above, methanol is coproduced. At least a portion of the methanol produced preferably is recycled to the process for producing the PVOH or PVOH copolymer, described above, e.g., to the alcoholysis of polyvinyl acetate or a copolymer of polyvinyl acetate to form PVOH or a PVOH copolymer. Additionally or alternatively, at least a portion of the methanol may be recovered as a saleable end product.

In embodiments where at least a portion of the methanol is recycled to the PVOH or PVOH copolymer synthesis step, at least a portion of any methanol stream may be treated in one or more purification steps, prior to being introduced into the reaction zone for synthesis of PVOH or PVOH (step (a)).

The hydrogenolysis step may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor, provided with a heat transfer medium, may be used. In many cases, the reaction zone may be housed in a single vessel or in a series of vessels with heat exchangers therebetween.

The catalyst may be employed in a fixed bed reactor, e.g., in the shape of a pipe or tube, where the reactants, typically in the vapor form, are passed over or through the catalyst. Other reactors, such as fluid or ebullient bed reactors, may be employed. In some instances, the hydrogenolysis catalysts may be used in conjunction with an inert material to regulate the pressure drop of the reactant stream through the catalyst bed and the contact time of the reactant compounds with the catalyst particles.

The hydrogenolysis reaction may be carried out in either the liquid phase or vapor phase. For example, the reaction may be carried out in the vapor phase under the following conditions. The reaction temperature may range from 75° C. to 350° C., e.g., from 125° C. to 350° C., e.g., from 150° C. to 325° C., from 150° C. to 300° C., or from 200° C. to 300° C. The pressure may range from 10 kPa to 10000 kPa, e.g., from 50 kPa to 5000 kPa, or from 100 kPa to 2500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenolysis step optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

In one embodiment, the molar ratio of hydrogen to methyl acetate that is introduced into the hydrogenolysis reaction zone is greater than 2:1, e.g. greater than 4:1, or greater than 12:1. In terms of ranges the molar ratio may be from 2:1 to 100:1, e.g., 4:1 to 50:1, or from 12:1 to 20:1. Without being bound by theory higher molar ratios of hydrogen to methyl acetate, preferably from 8:1 to 20:1, are believed to result in high conversion and/or selectivity to ethanol.

Contact or residence time may also vary widely, depending upon such variables as amount of methyl acetate, catalyst, reactor, temperature, and pressure. Typical contact times range from a fraction of a second to more than several hours when a catalyst system other than a fixed bed is used. Contact times, at least for vapor phase reactions, may be from 0.1 to 100 seconds, e.g., from 0.3 to 80 seconds or from 0.4 to 30 seconds.

The hydrogenolysis of methyl acetate to form methanol and ethanol is preferably conducted in the presence of a hydrogenolysis catalyst. Suitable hydrogenolysis catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA.

Particular hydrogenolysis catalysts include copper containing catalysts. These copper containing catalysts may further comprise one or more additional metals, optionally, on a catalyst support. The optional additional metal or metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Particular metal combinations for some exemplary catalyst compositions include copper/cobalt/zinc, copper/zinc/iron, copper/cobalt/zinc/iron, copper/cobalt/zinc/iron/calcium, and copper/cobalt/zinc/molybdenum/sodium. Particular copper containing catalysts may comprise copper chromite, copper and zinc, and/or copper-zinc-oxide. Exemplary catalysts are further described in U.S. Pat. No. 5,198,592, U.S. Pat. No. 5,414,161, U.S. Pat. No. 7,947,746, U.S. Patent Publication No. 2009/0326080, and WO 83/03409, the entireties of which are incorporated herein by reference. Hydrogenolysis catalysts may comprise CuO or ZnO. However, CuO and ZnO may be reduced or partially reduced by hydrogen during the course of the hydrogenolysis reaction. It is also possible to pre-reduce CuO and/or ZnO by passing hydrogen over the catalyst before the introduction of the methyl acetate feed.

As indicated above, in some embodiments, the catalyst further comprises at least one additional metal, which may function as a promoter.

In addition to one or more metals, in some embodiments of the present invention the catalysts further comprise a support or a modified support. As used herein, the term "modified support" refers to a support that includes a support material and a support modifier, which adjusts the acidity of the support material.

In particular, the hydrogenolysis of methyl acetate may achieve favorable conversion of methyl acetate and favorable selectivity and productivity to methanol and ethanol. For purposes of the present invention, the term "conversion" refers to the amount of methyl acetate in the feed that is converted to a compound other than methyl acetate. Conversion is expressed as a mole percentage based on methyl acetate in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for methanol/ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted methyl acetate. It should be understood that each compound converted from methyl acetate has an independent selectivity and that selectivity is independent from conversion. For example, if 60 mole % of the converted methyl acetate is converted to ethanol, we refer to the ethanol selectivity as 60%. The catalyst selectivity to each of methanol and ethanol may be, for example, at least 60%, e.g., at least 70%, or at least 80%. For example, the selectivity to methanol and/or ethanol may be at least 80%, e.g., at least 85% or at least 88%. Preferred embodiments of the hydrogenolysis process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the methyl acetate passed over the catalyst is converted to alkanes, which have little value other than as fuel.

The term "productivity," as used herein, refers to the grams of a specified product, e.g., ethanol, formed during the hydrogenolysis based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is possible. In terms of ranges, the productivity may be from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude alcohol product produced by the hydrogenolysis process, before any subsequent processing, such as purification and separation, will typically comprise methanol, ethanol and, possibly, water. The product stream from the hydrogenolysis reaction zone may also comprise unconverted methyl acetate. This unconverted methyl acetate may be separated from methanol and ethanol and saponified, for example, at room temperature with caustic on a stoichiometric basis. When aqueous sodium hydroxide is used as the caustic, the saponification product will comprise sodium acetate in aqueous solution. Caustic may be recovered, for example, by using a bipolar membrane. Sodium acetate may be converted to acetic acid by adjustment of pH. Caustic may be recycled to the saponification reaction zone. Acetic acid may be recycled to a reaction zone for converting acetic acid into vinyl acetate, which may be in turn polymerized.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product.

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which are incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

Example 1

A distillation was conducted using streams from a PVOH process. In the laboratory, a 40 tray Oldershaw column was employed. A mother liquor stream containing 0.24 wt % solids was fed about midway on the column, while an aqueous methanol stream containing 0.13 wt % solids was fed to the column about one third from the base. In the atmospheric distillation the overhead and the base temperatures were 68° C. and 100° C., respectively. The mother liquor feed rate was 13.7 g/min and the aqueous methanol feed rate was 11.5 g/min. The reflux ratio was maintained at about 0.23. No foaming or major fouling problems in the reboiler were observed during the distillation. Dark brown/black staining or fouling was observed from around tray 15 to the base. However, this minor fouling did not plug the small tray holes or downcomers of the Oldershaw column. The trays above the mother liquor feed were clean.

The analysis of the feed, overhead methanol/methyl acetate product, and the wastewater residue is given in Table 1 below.

TABLE 1

Analysis of laboratory experiment on distillation of feed/methyl acetate mixture

| Component | Mother Liquor Feed | Aqueous Methanol Feed | Product | Residue |
|---|---|---|---|---|
| Water (wt %) | 21.4 | 82.5 | 5.3 | 100 |
| Methanol (wt %) | 55.3 | 17.5 | 66.8 | 0.0656 |
| Methyl Acetate (wt %) | 27.1 | Nd | 27.9 | Nd |
| Ethanol (ppm) | 1476 | 75 | 1704 | Nd |
| Acetone (ppm) | Nd | Nd | Nd | 16 |
| Dimethyl Acetal (ppm) | 17 | Nd | 22 | Nd |
| Ethyl Acetate (ppm) | 315 | Nd | 366 | Nd |
| Acetaldehyde (ppm) | 248 | Nd | 313 | Nd |
| Toluene (ppm) | Nd | Nd | 74 | Nd |
| Acetic Acid (ppm) | 45 | Nd | Nd | 87 |
| Alkanes (ppm) | <100 | 781 | 3 | 932 |

Nd = non-detected, values are not normalized.
Product = Methyl Acetate, Methanol Product of Invention.

This Example illustrates that a methanol/methyl acetate stream could be purified at a low reflux ratio with less than 1000 ppm methanol and less than 2600 ppm alkanes in the waste water.

Example 2

Prophetic

This Example describes hydrogenolysis of methyl acetate as reported in paragraph of U.S. Patent Publication No. 2009/0326080. Methyl acetate is maintained as a liquid at 20° C., is pumped at a pressure from 10 to 50 atm, through a heat exchanger that vaporizes it completely at a temperature from 150° C. to 225° C. Preheated hydrogen at the same temperature range is added to the vapors as they exit from the heat exchanger. The molar ratio $H_2$ to methyl acetate is from 5 to 10. The hot mixture is blown through a catalytic bed including a CuO/copper chromite, a CuO/ZnO/$Al_2O_3$, or a CuO/ZnO/ activated carbon catalyst and an inert solid which acts as a diluent of the catalyst. The CuO is reduced to Cu by adding a mixture of $H_2$ and $N_2$ prior to adding any acetate. The CuO is thus reduced to Cu, the active form in the hydrogenolysis reaction. The reduction is carried out until no water is produced. The exothermicity of the reduction of the CuO is controlled by keeping the $H_2$ concentration in the gas mixture at levels not exceeding 5 vol. %. For the hydrogenolysis, the liquid hourly space velocities (LHSV) are from 1 to 10 h$^{-1}$ relative to the methyl acetate flow rates and to the true volume occupied by the catalyst (with no inert solid present). Temperature of the reactor is maintained from 225° C. to 275° C. The conversion of 1 mole of methyl acetate into 0.90 mole of methanol and 0.90 mole of ethanol is carried out within the above mentioned operating parameters. The unconverted methyl acetate, 0.10 mole, is separated from the methanol and ethanol products, and is recycled to the hydrogenolysis reaction.

Example 3

This Example also describes hydrogenolysis of methyl acetate. Six experiments were conducted in a Rotoberty® continuous stirred-tank reactor (CSTR). The same charge of 40 mL of a copper-zinc oxide on alumina catalyst, i.e. Mega-Max 700® (Süd Chemie), was used for all six experiments. The first four experiments were performed at ~360-375 psig, and the last two were at a higher pressure of 625 psig. At 360 psig, two reactions were tested at 250° C. followed by two at 275° C.; one temperature of 250° C. was tested at 625 psig. For all six experiments, the methyl acetate LHSV alternated between 0.85 hr$^{-1}$ and 1.25 hr$^{-1}$, and the $H_2$ to methyl acetate ratio was kept constant at approximately 14:1 $H_2$ to methyl acetate mole ratio.

The reaction conditions and results for the six methyl acetate experiments are provided in Table 2. A summary of the product composition for experiment 2 is provided in Table 3.

In Table 2, calculations are made for methyl acetate conversion, selectivity to methanol, selectivity to ethanol and productivity to ethanol.

Methyl acetate conversion is calculated as $(X_1$ minus $Y_1)*100 \div X_1$, where $X_1$ is the number of moles of methyl acetate (MeOAc) in the feed, and where $Y_1$ is the number of moles of methyl acetate in the product. Methyl acetate conversion is also referred to herein as $X_{MeOAc}$.

Selectivity to methanol is calculated as $X_2*100*2*Y_2$, where $X_2$ is the molality of methanol in the liquid product (i.e. moles of methanol per kg of sample), and where $Y_2$ is the molality of the total major liquid products. Such total major products include ethanol, methanol, ethyl acetate, butanols, $C_3$ ketone and alcohols, and heavy ends (MW≥116). The molality of methanol in the liquid product is multiplied by 2 in order to reflect that one mole of methyl acetate breaks into two components on the surface of the catalyst, and only half of the original molecule (the —$CH_3O$ group) reacts to form methanol. Selectivity to methanol is also referred to herein as $S_{MeOH}$.

Selectivity to ethanol and ethyl acetate is calculated as $[(X_3*2)+Y_3]*100 \div Y_2$, where $X_3$ is the molality of ethanol, where $Y_3$ is the molality of ethyl acetate, and where $Y_2$ is the molality of the total major liquid products. This value represents both free and esterified ethanol. Selectivity to ethanol and ethyl acetate is also referred to herein as $S_{EtOH+EtOAc}$.

Productivity to ethanol represents the grams of ethanol produced per kilogram of catalyst per hour. Productivity to ethanol is calculated as $(X_4$ minus $Y_4) \div Z_4$, where $X_4$ is grams of ethanol in the product per hour, where $Y_4$ is grams of ethanol in the feed per hour, and where $Z_4$ is kg of catalyst.

TABLE 2

Methyl acetate reaction conditions and key results

| | Experiment No. | | | | | | |
|---|---|---|---|---|---|---|---|
| | 1 | 2 | 3 | 4 | 5 | 6 | Average |
| Catalyst volume (ml) | 40 | 40 | 40 | 40 | 40 | 40 | |
| Catalyst charge (g) | 38.72 | 38.72 | 38.72 | 38.72 | 38.72 | 38.72 | |
| LHSV (hr$^{-1}$) | 0.85 | 1.27 | 0.88 | 1.29 | 0.82 | 1.24 | |
| MeOAc feed rate (ml/mm) | 0.57 | 0.84 | 0.59 | 0.86 | 0.55 | 0.82 | |
| $H_2$/MeOAc mole ratio | 13.9 | 14.1 | 13.5 | 13.8 | 14.4 | 14.4 | |
| $H_2$ feed rate (sccm) | 2232 | 3348 | 2232 | 3348 | 2232 | 3348 | |
| Reactor Pressure (psig) | 377 | 365 | 374 | 378 | 625 | 630 | |
| Reactor Temperature (° C.) | 249 | 250 | 274 | 274 | 251 | 251 | |
| $N_2$ sparge rate (sccm) | 100.06 | 100.06 | 100.06 | 100.06 | 100.06 | 100.06 | |
| GHSV (hr$^{-1}$) | 3739.2 | 5528.7 | 3746.0 | 5534.5 | 3730.5 | 5520.1 | |
| Residence time (sec) | 13.4 | 8.8 | 12.7 | 8.7 | 21.9 | 14.9 | |
| Motor speed (rpm) | 2020.0 | 2020.0 | 2003.0 | 2003.0 | 2003.0 | 2003.0 | |
| CondenserTemp (° C.) | 3.0 | 3.0 | 3.0 | 3.0 | 3.0 | 3.0 | |
| SampleTime (hr) | 2 | 2 | 2 | 2 | 2 | 2 | |
| Key Results | | | | | | | |
| Methyl Acetate Conversion (%) | 90.29 | 82.43 | 90.90 | 86.10 | 88.78 | 83.77 | 87.04 |
| Ethanol Selectivity (mol %)° | 81.05 | 78.55 | 67.26 | 71.12 | 75.07 | 71.59 | 74.11 |
| Methanol Selectivity (mol %) | 82.64 | 102.51 | 68.01 | 80.21 | 91.61 | 93.73 | 86.45 |
| Ethanol + Ethyl Acetate Selectivity (mol %) | 85.29 | 84.68 | 70.74 | 76.02 | 78.94 | 77.09 | 78.79 |
| EtOH Productivity, g EtOH/kg catalyst/hr | 373 | 489 | 321 | 471 | 328 | 442 | 403.9 |
| EtOH Productivity, g EtOH/L catalyst/hr | 361 | 473 | 311 | 456 | 17 | 428 | 391.0 |

TABLE 3

Methyl acetate product composition for Experiment 2.

| Total Output | grams | wt % | gmole |
|---|---|---|---|
| Hydrogen | 34.208 | 23.155 | 17.1039 |
| Oxygen | 0.000 | 0.000 | 0.0000 |
| Nitrogen | 19.794 | 13.398 | 0.7069 |
| Methane | 0.000 | 0.000 | 0.0000 |
| CO | 1.059 | 0.717 | 0.0353 |
| $CO_2$ | 0.000 | 0.000 | 0.0000 |
| Ethane | 0.318 | 0.215 | 0.0106 |
| Water (gas + liq) | 0.188 | 0.127 | 0.0105 |
| Acetaldehyde (gas + liq) | 0.263 | 0.178 | 0.0060 |
| Diethyl ether | 0.000 | 0.000 | 0.000 |
| Methanol (gas + liq) | 33.267 | 22.518 | 1.0383 |
| Ethanol (gas + liq) | 36.597 | 24.772 | 0.7956 |
| Acetone | 0.074 | 0.050 | 0.0013 |
| Methyl Acetate (gas + liq) ( . . . IPA) | 15.997 | 10.828 | 0.2159 |
| Unknown ($C_3$) | 0.026 | 0.018 | 0.0003 |
| n-Propanol | 0.058 | 0.039 | 0.0007 |
| Ethyl Acetate (gas + liq) | 5.468 | 3.701 | 0.0621 |
| 2-Butanone | 0.012 | 0.008 | 0.0002 |
| 2-Butanol (gas + liq) | 0.222 | 0.150 | 0.0030 |
| Acetic Acid | 0.000 | 0.000 | 0.0000 |
| 1-Butanol (gas + liq) | 0.052 | 0.035 | 0.0007 |
| Diethyl acetal | 0.000 | 0.000 | 0.0000 |
| Heavies | 0.132 | 0.089 | 0.0013 |
| Total Mass Out | 147.734 | 100.00 | 19.99 |

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

I claim:

1. A process for producing ethanol and a polymer or copolymer of vinyl alcohol, the process comprising the steps of:
   (a) contacting a vinyl acetate based polymer or copolymer with a base and methanol under conditions effective to form a polymer or copolymer of vinyl alcohol and a first stream comprising methyl acetate; and
   (b) reacting at least a portion of the methyl acetate with hydrogen to form methanol and ethanol.

2. The process of claim 1, further comprising the step of (c) recycling at least a portion of the methanol to the contacting step (a).

3. The process of claim 1, wherein the vinyl acetate based polymer or copolymer comprises polyvinyl acetate, and the polymer or copolymer of vinyl alcohol comprises polyvinyl alcohol.

4. The process of claim 1, wherein the vinyl acetate based polymer or copolymer comprises an alkene vinyl acetate copolymer, and the polymer or copolymer of vinyl alcohol comprises an alkene vinyl alcohol copolymer.

5. The process of claim 1, further comprising the steps of:
   (d) contacting acetic acid with reactants under conditions effective to form vinyl acetate; and
   (e) contacting the vinyl acetate with reactants under conditions effective to form the vinyl acetate based polymer or copolymer.

6. The process of claim 1, further comprising the step of purifying the first stream comprising methyl acetate from step (a) to form a second stream comprising methyl acetate.

7. The process of claim 6, wherein the purifying step takes place by one or more of the following techniques: extractive distillation, liquid/liquid extraction, distillation, crystallization, gas stripping, a membrane separation technique, filtration, flash vaporization, and chemical reaction of one or more impurities.

8. The process of claim 6, wherein the first stream comprises methyl acetate, methanol, light organics and water.

9. The process of claim 6, wherein the second stream comprises methyl acetate and methanol.

10. The process of claim 6, wherein the second stream comprises from 5 wt % to 95 wt % methyl acetate and from 5 wt % to 95 wt % methanol, based on the total weight of methyl acetate and methanol in the second stream.

11. The process of claim 6, wherein the second stream comprises from 60 wt % to 95 wt % methyl acetate and from 5 wt % to 40 wt % methanol, based on the total weight of methyl acetate and methanol in the second stream.

12. The process of claim 6, wherein the second stream comprises from 70 wt % to 90 wt % methyl acetate and from 10 wt % to 30 wt % methanol, based on the total weight of methyl acetate and methanol in the second stream.

13. The process of claim 6, wherein the second stream comprises from 90 wt % to 100 wt % methyl acetate and from 0 wt % to 10 wt % water, based on the total weight of methyl acetate and water in the second stream.

14. The process of claim 6, wherein the second stream comprises from 93 wt % to 100 wt % methyl acetate and from 0 wt % to 7 wt % water, based on the total weight of methyl acetate and water in the second stream.

15. The process of claim 6, wherein the second stream comprises from 95 wt % to 100 wt % methyl acetate and from 0 wt % to 5 wt % water, based on the total weight of methyl acetate and water in the second stream.

16. The process of claim 6, wherein the hydrogenolysis step (b) occurs in the presence of a catalyst.

17. The process of claim 16, wherein the catalyst is a copper containing catalyst.

18. The process of claim 1, wherein the hydrogenolysis step (b) forms a mixed alcohol stream comprising methanol and ethanol, the process further comprising the step of separating the mixed alcohol stream into a methanol stream and an ethanol stream.

19. The process of claim 18, wherein the ethanol stream comprises at least 90 wt. % ethanol.

20. The process of claim 18, wherein the methanol stream comprises at least 90 wt. % methanol.

* * * * *